United States Patent [19]

Hignett et al.

[11] Patent Number: 4,801,407

[45] Date of Patent: Jan. 31, 1989

[54] PROCESS FOR THE PRODUCTION OF A PEROXY COMPOUND

[75] Inventors: Geoffrey J. Hignett, Lymm; Iain S. MacKirdy, Warrington, both of England

[73] Assignee: Interox Chemicals Limited, London, England

[21] Appl. No.: 381,753

[22] Filed: May 25, 1982

[30] Foreign Application Priority Data

Jun. 10, 1981 [GB] United Kingdom ............... 8117841

[51] Int. Cl.$^4$ ............................................. C07C 178/00
[52] U.S. Cl. ..................................... 260/502 R; 8/111; 252/186.1; 252/186.26; 562/480; 562/590; 562/595
[58] Field of Search ....................................... 260/502 R

[56] References Cited

U.S. PATENT DOCUMENTS 2,284,477  5/1942  Reichert et al. ................. 260/502 R
4,385,008  5/1983  Hignett ............................ 260/502 R

FOREIGN PATENT DOCUMENTS 550490   1/1943  United Kingdom ............ 260/502 R
561180   5/1944  United Kingdom ............ 260/502 R
1041983  9/1963  United Kingdom ............ 260/502 R Primary Examiner—Werren B. Lone
Assistant Examiner—Vera C. Clarke
Attorney, Agent, or Firm—Larson and Taylor

[57] ABSTRACT

In the present invention, hydrated magnesium salts of the carboxylate group in certain aromatic or olefinically unsaturated peroxyacids such as monoperoxyphthalic acid or monoperoxymaleic acid are made by reacting the corresponding anhydride with aqueous hydrogen peroxide and a magnesium base, in the absence of a significant amount of free iron. By so doing, the process avoids the use of non-aqueous solvents such as ethyl acetate. Solid product can be obtained by using no more than enough hydrogen peroxide and water for solely a damp product to be obtained or by crystallization from an aqueous solution, preferably with recycle of the mother liquor. Preferably the reaction temperature is maintained at 5° to 25° C., employing 1.8 to 2.2 moles anhyhdride per mole of magnesium base, and 0.95 to 1.2 moles of hydrogen peroxide per mole of anhydride.

The product can be used as a bleach and as a disinfectant.

19 Claims, No Drawings

PROCESS FOR THE PRODUCTION OF A PEROXY COMPOUND

The present invention relates to a process for the production of a peroxy compound, and more particularly to the production of magnesium salts of peroxyacids.

In European patent application No. 80303457.8, publication No. 27693A, in the name of Interox Chemicals Limited, hereinafter referred to as EP No. 27693A, there is described and claimed:

In solid form, the magnesium salt of:

Class (1)-an aromatic carbocyclic compound substituted around the aromatic nucleus by a carboxylate group and a peroxycarboxylic acid group both groups being derivable from the corresponding aromatic carbocyclic anhydride by reaction with hydrogen peroxide, said aromatic carboxylic compound optionally being further substituted by at least one of the groups selected from alkyl, carboxylate, sulphonate, nitro, chloro and bromo groups or Class (2)-a cycloaliphatic compound substituted around the cycloaliphatic nucleus by a carboxylate group and a peroxycarboxylic acid group both groups being derivable from the corresponding cycloaliphatic carbocyclic anhydride by reaction with hydrogen peroxide, said cycloaliphatic carboxylic compound optionally being further substituted by at least one of the groups selected from alkyl, carboxylate, sulphonate, nitro, chloro and bromo groups or Class (3)-compounds other than those in class 1 in which the carbonyl group of the peroxycarboxylic acid substituent is conjugated with the carbonyl group of a carboxylate substituent via olefinic unsaturation which carboxylate and peroxycarboxylic acid substituents are derivable from the corresponding anhydride by reaction with hydrogen peroxide.

The application also described a method for the production of such magnesium salts in solid form in which the corresponding anhydride is reacted with hydrogen peroxide and a base, namely a magnesium compound in the presence of a solvent, namely a low molecular weight aliphatic ester, from which the resultant magnesium salt precipitates. In many respects, such a route is convenient, in that the preferred organic starting material, the anhydride is soluble to a considerable extent, whereas the resultant magnesium salt of the peroxyacid is substantially insoluble, in the non-aqueous solvent.

Now, it has long been recognised as a desideratum in many commercial processes to employ, where practicable, aqueous instead of non-aqueous routes. Accordingly an investigation into an aqueous route for producing the magnesium salts was set in motion. However, in the case of manufacturing organic peroxyacids and their salts, the tendency has been in the reverse direction. About 40 years ago Du Pont in British Patent Specification Nos. 550490 and 561 180 exemplified processes for the production of aqueous solutions of peroxyacids, including peracetic acid, monopersuccinic acid and monoperphthalic with sodium bicarbonate hydroxide or phosphate, borax or ammonium hydroxide but they did not produce any solid product. When Air Liquide about 20 years later in British Patent Specification No. 1041985 sought to produce crystalline alkali metal peroxyacid salts they changed to a non-aqueous route, quite possibly in view of the high solubility of such peroxyacid salts in aqueous media even at sub-ambient temperatures down to freezing point of the solution.

In the course of their investigations, the instant inventors had found that, in the manufacture of solid peroxy species from anhydrides and hydrogen peroxide, the results were not predictable on the basis of prior published material. Thus, for example, there was no uniformity in products obtained from acetic, succinic, or phthalic anhydrides which were a grouping of three anhydrides referred to by Du Pont. Reaction between $H_2O_2$, anhydride and magnesium base, in the mole ratio of 1:1:0.5 in the non aqueous conditions of aforementioned EP No. 27693A, produced the hydrated magnesium monoperoxyphthalate using the non-aqueous method described in EP No. 27693A, but there was no magnesium peroxyacetate solid and the solid obtained from succinic anhydride was disuccinyl peroxide (otherwise called disuccinic acid peroxide).

When an aqueous route for obtaining magnesium salts of carboxylate/percarboxylic acid compounds was employed, starting with phthalic anhydride and following the general method of Example 5 of EP No. 27693A, but substituting water for the non aqueous solvent, the resultant product contained little or no peroxyacid, either as such or as its magnesium salt. In itself, this was not so surprising, because the intended reaction involved the anhydride and the magnesium base, both of which were known to be substantially insoluble or only poorly soluble in aqueous media whereas the magnesium salt, were it to be produced, was known to be very soluble indeed. Insoluble reactants and soluble product, if formed, is a far from ideal recipe for producing the desired product, a salt of a carboxylic acid group but not a salt of the peroxycarboxylic group, readily in solid form. Moreover, there would be a tendency for peroxyacid in solution to react with further or hitherto unreacted anhydride to form a diacyl peroxide which is less soluble than the magnesium peroxyacid/carboxylate salt, as is believed to have happened in the formation of disuccinyl peroxide. It was therefore apparent to the inventors that the employment of magnesium base introduced heretofore unrecognised complicating factors.

Detailed further investigation indicated that a major factor was the presence of a certain contaminant in the reactants commercially available on a plant scale, even though the desired magnesium salt product could be made by the non-aqueous route using the same reagents. Furthermore, even when that factor had been overcome a disparity between the classes 1, 2 and 3 of magnesium salts described hereinbefore was found, in that solid product was not obtained by the instantly described process for all of them.

Various other publications, such as American patent specification Nos. 3384596 and 3563687 and Australian Patent Specification No. 36619, all assigned to the Dow Chemical Company, describe the addition of alkali metal or alkaline earth metal salts of acids, such as magnesium sulphate to solutions of various performed organic peroxyacids, the purpose being to activate these solutions for bleaching or to overcome fading of coloured fabrics during peroxyacid bleaching. Thus, none of these specifications teach the formation of solid peroxyacid salts nor do they indicate the problems or disparity in obtaining the solid salts nor do they show ways or overcoming those problems.

Accordingly, it is an object of the present invention to provide a process for the manufacture of certain of the aforementioned magnesium salts in solid form employing an aqueous reaction medium, that avoids or mitigates the effect of the contaminant.

According to the present invention there is provided a process for the production of hydrated magnesium salts in solid form of classes 1 and 3 described hereinbefore in which the corresponding anhydride and magnesium base are brought into contact with an aqueous medium comprising hydrogen peroxide and water, in such an amount that at least some hydrated magnesium salt of the peroxycarboxylate precipitates therefrom, the reaction being conducted in the presence of no free iron or less than a significant amount of free iron in the reaction mixture.

In the course of investigating the process of the present invention, it was found that the presence of significant amounts of iron could result in a product devoid of or very low in active oxygen, whereas when the same amounts were present in the non-aqueous route in EP No. 27693A, the product had a very much higher active oxygen content. It is to be understood that the present invention is not dependent upon the explanation that is given hereinafter. It would appear that important sources of iron contamination are especially the magnesium base and the phthalic anhydride, and another is any aqueous phase that is recycled. It is believed that the magnesium causes polarisation of the hydrogen peroxide and when both are adjacent to the anhydride, reaction occurs that leads to opening of the anhydride ring formation of a peroxyacid group the magnesium salt of the carboxylate group being formed. It is believed that the presence of a significant amount of free iron in the vicinity of the magnesium can interfere, and can thus result in the decomposition of the hydrogen peroxide or the peracid during its formation. It is obviously sensible to monitor the iron content of the base and any aqueous phase added or recycled and for safety's sake the anhydride as well.

For advantageous application of this process, the magnesium base employed preferably has no more than a low impurity content of iron, of which a preferred range of concentrations is from 0 to $25 \times 10^{-6}$ especially not above $15 \times 10^{-6}$ moles of iron per mole of magnesium base. In practice, it has been found that the reaction is generally tolerant to the concentrations of iron in commercially available anhydrides tried so far. However, as the concentration of iron in the aqueous phase and the solid reactants, especially the magnesium base increases above the specified ranges, approaching the amount at which it is significant, the tendency for the iron to interfere with the intended reaction increases. Thus, it is possible to employ magnesium bases and aqueous phase that contain from 25 to $45 \times 10^{-6}$ moles of iron per mole of magnesium base, but there is an increasing likelihood that post-production and pre-separation decomposition may occur at the higher iron content. In such an intermediate range of iron contents, it is desirable to separate the product from any mother liquor quickly, by selecting reaction periods at the low end of the ranges given subsequently herein and by using rapid solid:liquid separators, and preferably within 125 minutes from beginning to introduce the solid reactants. A convenient method of determining whether or not excess iron is present in, for example, the production of MMPP, is to observe the colour of the aqueous phase. If it has a pinkish hue, a significant amount of free iron is present, as e.g. when magnesium oxide containing 150 ppm iron is used. For the avoidance of doubt, it is to be understood that when reference herein is made to the amount of iron that is present in the reaction medium, this refers to free or available iron, that is to say iron that is not sequestered, and reference to ppm is on the basis of weight/weight. It will naturally be recognised that by the addition of for example EDTA or like chelating agent to a reaction mixture containing a significant or intermediate amount of free iron, the deleterious effect of the iron can be ameliorated. In effect, such additions reduce the free iron content to within the desired range.

Typically, the principal contaminant encountered heretofore in the reactants has been iron but the same considerations apply mutatis mutandis to other catalytic transition metals such as copper, cobalt and vanadium, if they are encountered additionally or instead of the free iron.

As described in the aforementioned European patent application, when the magnesium salt of peroxycarboxylic acid compound in classes 1, or 3 herein is formed, it is hydrated and in general, the salt is formed from the carboxylic acid group, i.e. the carboxylate group and not from the peroxycarboxylic acid substituent, which latter remains intact. Similarly, the anhydrides that were described in said European patent application for use in the formation of the magnesium salts in classes 1 and 3 can also be used likewise in the process of the instant invention.

Even when the contaminant problem controlled, as for classes 1 and 3, the inventors were not able to obtain a solid peroxyacid/magnesium salt product from class 2 of EP No. 27693A or from succinic anhydride. When conditions were employed in which a solid was obtained, it was essentially devoid of peroxyacid, and where higher volumes of aqueous medium were used initially, followed by further additions of solid reagents and concentrated hydrogen peroxide the resultant solution merely become an increasingly viscous treacle that did not yield the designed solid peroxyacid salt even on cooling and seeding.

The correspondence between the anhydride and the resultant peroxy compound derived from it is readily understood from the fact that perhydrolysis of the anhydride results in formation of a peroxycarboxylic acid group and a carboxylic acid group. The other substituents, if any from the list of alkyl, carboxylate, sulphonate, nitro, chloro and bromo groups remain throughout the reaction in the same relative positions around the aromatic nucleus. However, it will further be recognised that where the anhydride starting material contains one or more of the aforementioned other substituents, the resultant product is often a mixture of isomers. Thus, for example, the magnesium salt obtained using trimellitic anhydride as starting material is a mixture, it is believed, of the magnesium salt of benzene-1,3-dicarboxylate-4-peroxycarboxylic acid and benzene-1,4-dicarboxylate-3-peroxycarboxylic acid and the magnesium salt falls within class 1. Further examples within class 1 include the product obtained using pyromellitic anhydride as starting material and in this case the product is again a mixture of isomers comprising benzene-1,4-dicarboxylate-2,5-diperoxycarboxylic acid and benzene, 1,5-dicarboxylate-2,4-diperoxycarboxylic acid. Desirably, for the production of class 1 compounds, any nitro, chloro or bromo substituent is meta to one of the carbonyl groups in the anhydride and para to the other. Where the additional substituent around the benzene nucleus is an alkyl group, it can be short chain, for example methyl, ethyl or propyl up to a long chain hydrophobic substituent such as dodecyl, hexadecyl, or octadecyl. Conveniently the alkyl substituent can be in any position relative to the carbonyl groups of the anhydride group in the starting material.

One specially suitable and convenient starting material is phthalic anhydride, the product formed from which is magnesium monoperoxyphalate, a member of class 1, which has the formula, expressed in anhydrous form, of:

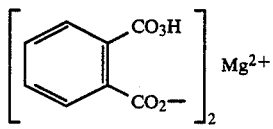

and when it is produced in solid form is hydrated, generally containing in the region of 5 to 8 moles of water per mole of the magnesium salt when dry. Analysis has shown the presence of hexa-aquo magnesium ions. Similarly, the solid products obtained using the other anhydrides as starting material are also obtained in hydrated form from a process of the instant invention.

It will be recognised that suitable starting materials to produce magnesium salts within class 3 are olefinically unsaturated aliphatic acid anhydrides and they include maleic anhydride and corresponding compounds in which the olefinic group is further substituted by an alkyl group which can be selected from the same group as for class 1, e.g. citraconic anhydride up to a total $C_{20}$ carbon content. Consequently, the resultant product is an olefinically unsaturated alphatic compound substituted by a carboxylate group and a peroxycarboxylic acid group, the carbonyl group of the carboxylate substituent being conjugated with the carbonyl group of the peroxycarboxylic acid via the olefinic unsaturation within the aliphatic compound, both substituents being derivable from the starting material by reaction with the hydrogen peroxide.

For convenience, the production of magnesium salts in classes 1 and 3 is described hereinafter with reference specifically to the production of magnesium monoperoxyphthalate, referred to for brevity as MMPP, but it will be recognised that the general method can be employed mutatis mutandis employing the other anhydrides as starting materials. By way of guidance it will be understood that, for example, where the anhydride is substituted by one or more carboxylic groups, a pro rata increase in the mole ratio of magnesium compound to the anhydride will allow for the extra carboxylic acid group, and where the anhydride contains more than one anhydride group, a pro rata increase in the ratios of both the hydrogen peroxide and magnesium base to the anhydride will allow for this. Reference herein to any mole ratio includes a reference to the pro rata mole ratio when an anhydride containing more than one anhydride group or one or more extra carboxylic acid groups is used. In addition it will be recognised that the resultant solid that is isolated can also contain a proportion of non peroxygenated magnesium salt and that this proportion can vary, to some extent, depending upon the starting materials the relative mole ratios of the starting materials and the process conditions.

The magnesium base employed to form the salt is a compound that has a $pK_a$ higher than that of the carboxylic acid group in the classes 1, and 3 described hereinbefore. In practice, this means that for all the salts it is possible to employ as the magnesium base, magnesium oxide, magnesium hydroxide, magnesium carbonate and basic magnesium carbonates, all of which are water-insoluble to a great extent but that it is possible in some cases to employ the magnesium salt of certain carboxylic acids and in particular magnesium acetate when the $pK_a$ of the carboxylic acid in the class 1, or 3 compound is 4.7 or lower, e.g. monoperoxyphthalic acid. Bases such as magnesium acetate exhibit greater solubility in aqueous media, but it is often more convenient to employ an oxide, hydroxide or carbonate as the base because there is substantially no residual base-derived contaminant in the final solid product.

It is convenient to employ both the anhydride and the magnesium base in particulate form, and in many cases that which is available commercially. The average flake, powder or droplet particle size of the anhydride is generally selected in the range of from 0.01 mm to 5 mm and in practice often falls within the range of 0.03 mm to 1 mm, and that of the magnesium base is normally below 0.5 mm, and often from 0.005 mm to 0.25 mm. In general, it will be understood that the reaction between hydrogen peroxide and the anhydride is exothermic and that the rate of reaction can be controlled to a certain extent by selection of the particle size of the anhydride, the larger that the average particle size is, the slower the rate, but the effect can be counter-balanced by a change in the rate of introduction of the anhydride into the peroxide, a slower rate of introduction balancing a small particle size. A rate of reaction that is too fast can lead to difficulties in controlling the exotherm, especially when the amount of aqueous hydrogen peroxide solution employed is such that it is taken up completely by the reactants in the course of the reaction, producing a damp solid, which is substantially free from a continuous liquid phase. In practice, an increase in the average particle size of the anhydride tends to increase the likelihood of the solid product containing a residual amount of unreacted anhydride.

The anhydride is preferably employed in a mole ratio to the magnesium base of from 1.5:1 to 2.5:1, and in several embodiments from 1.8:1 to 2.2:1. Where the equivalent mole ratio of anhydride to magnesium base falls to below 1:5:1, there is an increased tendency for the peroxidic species in the reaction medium and mother liquor to decompose with loss of Avox from the system, whereas where the equivalent mole ratio volume 2.5:1. there is a much increased chance that the product would contain detectable levels of anhydride, which would make that product less acceptable for its intended use.

The hydrogen peroxide is added desirably in an equivalent mole ratio to the anhydride, typified by phthalic anhydride, of at least 0.7:1, preferably in a mole ratio of at least 0.9, normally not more than 5:1, in many cases not more than 2:1 and most preferably in the range of 0.95:1 to 1.2:1. It will be recognised that the perhydrolysis reaction, i.e. the reaction between hydrogen peroxide and the anhydride can be regarded as in competition with hydrolysis of the anhydride which would also occur under aqueous alkaline conditions to a greater or lesser extent. We have found that employment of a hydrogen peroxide to anhydride mole ratio of at least 0.9:1, and especially at 0.95 or higher permits the resultant product to contain the perhydrolysis product, the peroxyacid compound, in a high ratio to the hydrolysis product, a dicarboxylic acid, even when a substantial excess of water is present. Such a product can be recognised by an avox of at least 5% and preferably at least 5.8%, w/w. It will be recognised that the hydrogen peroxide can be employed in a mole ratio to anhydride in excess of 2:1, but that under such circumstances, a substantial residuum of hydrogen peroxide remains at the end of the reaction. After augmentation with fresh hydrogen peroxide, if or when necessary, it is particularly desirable to recycle any separable aqueous solution, which in practice contains magnesium, peroxyacid and hydrogen peroxide and elsewhere is called mother liquor, thereby avoiding to a considerable extent the loss of active oxygen and other reagents that would otherwise occur.

It will further be recognised that where it is desired to produce or one can tolerate a product that contains a substantial proportion of non-peroxygenated compound or diacyl peroxide, a mole ratio of hydrogen peroxide to anhydride of below 0.7:1 can be employed. Thus, for example, at a mole ratio of 0.5:1 of hydrogen peroxide to phthalic anhydride, there is an increased tendency for the resultant product to contain in addition to some MMPP, some diacyl peroxide, some magnesium phthalate and some residual phthalic anhydride.

In addition to the hydrogen peroxide, it is necessary, in order to obtain crystallisation of the hydrated product, to carry out the reaction in the presence of at least a minimum amount of water, which in practice is at least 6 moles of water per mole of magnesium salt obtained, including any water that may be generated from the acidification of the magnesium base. In this context magnesium oxide and carbonate generate 1 mole of water for each mole of oxide or carbonate consumed, magnesium hydroxide generates two, basic magnesium carbonate between one and two depending upon its basicity, but acetate generates none. The solid dried magnesium salt generally contains water in a ratio to magnesium ion in the range of 5 to 8:1 and often 6:1. It is possible to produce solely a damp solid as the reaction product, with no separate and distinct liquid phase. Since also a small amount of liquid can adhere to the surface of crystals, the liquid phase-free product can be obtained using equivalent mole ratios of (a) anhydride, (b) hydrogen peroxide and (c) total water each to the magnesium base respectively of 1.5 to 2.5:1, 1.5 to 3.0:1, and 5 to 12:1. When more aqueous phase is employed, relative to the amounts of anhydride and magnesium base, a separable aqueous phase (mother liquor) remains at the end of the reaction. In practice, the weight ratio of total solid starting materials, namely the anhydride calculated as phthalic anhydride and the magnesium base calculated as magnesium oxide to the aqueous phase is normally not less than 100 g per 1000 g of aqueous phase, to obtain solid product, and generally is from 200 g to 1500 g per 1000 g of aqueous phase. When mother liquor is reused, the solids addition is less to obtain the same weight of product than when fresh aqueous solution is used, often being from 110 to 500 g per 1000 g aqueous phase on the aforementioned basis.

In one practical method of operation, it is often convenient to produce an aqueous slurry having a separable solids content, when dry, of from 15% to 45% by weight. The separated solids can be dried and the mother liquor recycled.

The solids can be separated from the saturated aqueous solution employing standard solid:liquid separators such as drum or plate filters or centrifuges, producing often a damp cake containing 5% to 30% by weight of retained mother liquor. The separated mother liquor is preferably analysed to determine the residual concentration of peroxyacid, hydrogen peroxide and magnesium therein, and in the light of the analysis, addition of appropriate amounts of the starting materials including water, to restore the ratios of anhydride, total active oxygen (provided by hydrogen peroxide and peroxy compounds) and magnesium to the desired amounts and ratios calculated. A convenient way of operating is to produce approximately the same amount of product each cycle so that the same amounts of reactants can be added each cycle, analysis being carried out periodically by way of confirmation. Broadly speaking, it has been found that it is desirable to employ ratios of anhydride, peroxide and magnesium base in subsequent cycles within the preferred ranges of ratios described for the initial cycle and that losses of active oxygen from the system in the course of the reaction tend to vary in line with the temperature of the reaction, most satisfactory avox losses of below 10% being achievable at around ambient temperature, e.g. 10° to 25° C., despite the fact that the mother liquor is a saturated solution of the magnesium peroxyacid/carboxylate compound. Moreover, recycling using the same recycle conditions each time can result in a substantially steady state for the product and mother liquor, including acceptably low iron contents.

In recycling, it is often most convenient to select mole ratios for the reactants which take into account the content of the recycled mother liquor, and are within the mole ratios of hydrogen peroxide:anhydride of 0.95:1 to 1.1:1 and of anhydride to magnesium base selected from magnesium oxide, hydroxide and carbonates of from 1.8:1 to 2.2:1, together with enough water to replace that removed in the crystallate. It will be recognised that a mole of peroxyacid in solution is equivalent to a mole of each of hydrogen peroxide and anhydride being present. When it is desired to produce a dry weight of product per cycle which amounts to 15% to 45% by weight of the reaction mixture, in the desired mole ratios of reactants, as aforementioned, the weight of solids and liquids make-ups are generally selected within the ranges 12% to 50% for solids and 6% to 50% for liquids, each based upon the weight of recycled mother liquor plus liquids make-up. Preferably, the amounts of make-ups are selected in step with each other, the larger the amounts, the more product obtained, but there is a second factor for the liquids. As the efficiency of separation of solid from liquid falls in the preceding cycle, the amount of liquid make-up needed to restore the reaction mixture to the composition of the preceding cycle rises. Thus, desirably, at a 5% by weight liquid retention in the separated solids, approximately the same weights of solids and liquids make-ups is used, rising to a weight ratio of liquids to solids make-ups of about 2:1 at a liquid retention of 30%. Interestingly, the preferred concentration of hydrogen peroxide in the liquids make-up varies in an inverse relationship to the retention of liquid in the preceding solid-liquid separation, rising progressively from 20%±2.5% w/w at a liquids retention of 30% to 40%±4% at liquids retention of 30%, but it is broadly independent of the amount of product produced per cycle, assuming that it is used in the most preferred range of mole ratios.

In one convenient method, a premixture of both solid starting materials in the correct proportions is introduced into the aqueous liquid phase comprising hydrogen peroxide and water and/or recycled mother liquor.

However, alternative arrangements for bringing the solid and liquid phases into contact can be employed. Thus, for example, it is possible to add the solid components separately to the liquid phase, such as first adding the anhydride and then the magnesium base or to form a slurry of the solid starting materials or each separately, with only a part of the aqueous phase and subsequently introduce the slurry into the rest of the aqueous phase, care naturally being taken to avoid a slurry containing the anhydride, the magnesium compound and water in the absence of hydrogen peroxide. Molten anhydride can be introduced as a stream into the aqueous phase and reduced to droplets in situ by the stirring. The base can be added separately either simultaneously or subsequently. Alternatively, it is possible to introduce the aqueous hydrogen peroxide solution or a more concentrated hydrogen peroxide solution and water separately into an agitated bed of solids. Finally the liquids and solids in the desired mole ratios can be fed simultaneously into a reaction vessel, possibly into a residual amount of reaction mixture to top up the amount of reaction mixture to a desired level after a predetermined fraction has been removed, for example from 5 to 50%. In order to reduce to a minimum the extent to which a reacted anhydride can remain within the product, it is highly desirable to continue mixing the reaction mixture thoroughly throughout the course of the introduction of the reagents and any subsequent reaction or digestion periods.

The reaction can be carried out conveniently at any temperature above the melting point of the aqueous phase up to that at which increasing losses of peroxidant from the system render the process less attractive. In practice, it is advisable to maintain the temperature of the reaction mixture at not greater than 40° C. and preferably at not greater than 30° C. An especially preferred range of temperature for the reaction is from 5° to 25° C. In view of the fact that the reaction is exothermic, in general, cooling of the reaction mixture is required in order to prevent the temperature rising unduly even where it is desired to maintain a reaction temperature above ambient, although some control of the temperature can be effected by controlling the rate at which the reactants are brought into contact with each other. In practice, external cooling of the reaction vessel is desirable, for example by a cooling jacket around the vessel and/or pumping the reaction mixture through a heat exchanger and/or by locating within the reaction vessel bundles of tubes through which cooling fluid circulates. If desired, at the end of the reaction period, the temperature of the reaction mixture or the mother liquor after separation from the precipitate can be lowered so as to promote further crystallisation of the magnesium salt from solution, for example by 5° to 20° C. By way of example, the reaction mixture or mother liquor in the range of 10° to 25° C. can be cooled to a temperature in the range of 3° to 15° C., or to a greater extent, e.g. up to 25° C. cooling, if the aqueous phase contains at the end of the reaction period an appreciable quantity of an antifreeze, such as ethanol or di or triethylene glycol, all of which are recognised as being miscible entirely with water. The aqueous phase conveniently, can contain a small proportion of a miscible liquid anti-foaming agent such as isopropanol which can function also as an antifreeze in an amount of up to 10% by weight, and/or a trace amount e.g. up to 0.5% by weight of an immiscible compatible commercial antifoaming agent.

Desirably, the reaction period, including the period during which the reagents are being brought into contact with each other and any period subsequent thereto before the crystalline magnesium salts are separated from the supernatent liquor, lasts at least 20 minutes and in general practice not longer than 5 hours. Preferably, the total reaction period is selected within the range of up to 150 minutes and often from 30 to 150 minutes. Within that total reaction period, the reagents are often brought into contact during a period of from 20 to 120 minutes and the post introduction period comprises the remainder, which is often selected within the range of from 5 to 120 minutes. It will be recognised that these range are particularly appropriate for batch reaction and processes in which the aqueous phase is recycled in a batch fashion. By way of guidance, it will be understood that the practical period for introduction of the solids tends to be longer in larger scale operations. For example, a typical laboratory scale period for solids introduction of about 10 to 20 minutes typically becomes on a plant scale 25 to 80 minutes. Where it is desired to carry out the reaction on a continuous basis, it will be understood that the reactants and any recycled aqueous phase will be fed into the reaction vessel at the rate appropriate to provide a mean residence time of at least 10 minutes to 5 hours, and in many cases from 15 minutes to 150 minutes. Naturally, the selection of reaction temperature and reaction period/residence times are in practice considered together, shorter reaction periods being associated with the higher reaction temperatures and vice versa.

In order to encourage the magnesium salt to precipitate out of solution it is possible in theory to introduce, at the end of the reaction, an appropriate quantity of a water soluble magnesium base such as magnesium acetate, or a salt that after deposition onto the peroxyacid salt would act as a desensitising agent, i.e. assist the peroxyacid salt to resist even better the effects of thermal and impact shocks. Such a salt of magnesium is magnesium sulphate. It is often more convenient to reduce the overall losses arising because some of the magnesium salt of peroxyacid remains in solution, by recycling that aqueous solution and after make-up with peroxide and water, as needed, introducing thereinto further amounts of anhydride and magnesium base.

When the magnesium salt has been separated from its supernatant liquor, it can, if desired, be washed with a solvent in which the magnesium salt is insoluble to remove absorbed/adsorbed water and hydrogen peroxide, which solvent in practice is often a low molecular weight ester of an aliphatic acid, containing from 3 to 10 carbon atoms of which a good example is ethyl acetate. Additionally or alternatively, it can be washed with a chlorinated hydrocarbon such as chloroform or ethylene dichloride to remove residual anhydride. A convenient amount to employ is from 5 to 50% by weight of the magnesium salt. Naturally, use of either of them can be avoided if analysis of the magnesium salt before washing indicates that there is no detectable anhydride present, and as it has been mentioned before, such a beneficial state of affairs can be encouraged by employing sufficient magnesium base in relation to the anhydride as in the most preferred mole ratio range of magnesium base to anhydride.

The reaction and separation can conveniently be carried out in apparatus made from stainless steel or glass or tantalum or other material employable for peroxidic substances. Stainless steel appears not to introduce any significant amount of free iron or any other catalytic ion into the reaction medium.

Advantageously, by producing the magnesium salt of the peroxyacid in a medium in which it is soluble to a substantial extent, it has been found that it is possible to produce crystalline material of larger crystal size than when it was produced in a non-aqueous liquid such as ethyl acetate in which it was soluble to only a very restricted extent. This is of considerable benefit in that it enables the solid to be separated more readily from the liquid phase and to reduce the number or extent of operations required to produce a particle size range suitable for incorporation in washing or bleaching compositions, compatible size ranges with the other components being achieved more readily. In addition to being incorporated in washing and/or bleaching compositions, the product of the invention can be used for disinfection of aqueous media and in solution, of solid surfaces, such as metals, plastics, ceramics, wood and glass, in the general molar amounts applicable to the use of the peroxyacid of which it is a salt.

Having described the invention in general terms, specific embodiments will now be described more fully by way of example only. Variations in accordance with the foregoing description and obvious modifications can be made without departing from the point of the invention.

EXAMPLES 1–16

In Examples 1 to 13, the magnesium salt of monoperoxyphthalic acid was obtained by reacting together a premix of particulate phthalic anhydride (15.05 g, 0.1017 mole) and the weight of particulate magnesium oxide specified in Table 1, with an aqueous solution of hydrogen peroxide obtained by diluting 50% w/w hydrogen peroxide (6.90 g, 50%, 0.1014 mole of $H_2O_2$) with the additional amount of water (DMW) specified in Table 1. The solid pre-mix was introduced slowly into the aqueous hydrogen peroxide solution over a period of 10 minutes, and the reaction mixture was maintained at the temperature specified in Table 1 ±1° C. by cooling it in a constant temperature enclosure, and the mixture was constantly stirred throughout the introduction and post-introduction reaction periods. The appearance of the mixture was monitored, and when to the eye it had ceased to become thicker, which occured generally about 10 to 20 minutes after all the reagents had been mixed together at 20° C. or higher and after a little longer at 10° C., The reaction mixture was then cooled to 5° C. and filtered under vacuum. The solid filter cake was washed with a small volume of ethyl acetate and was then dried in a vacuum dessicator over phosphorus pentoxide. The dried product and the filtrate were then analysed by the following standard methods in all the Examples:

Avox-total by titration of liberated iodine against thiosulphate.

Avox-hydrogen peroxide by titration against ceric sulphate using ferroin as indicator.

Avox-peracid by difference between the two previous results.

Magnesium by EDTA titration with solochrome black as indicator at pH 10. The results are summarised in Table 2.

The infra red spectrum of the product was also measured, and therefrom the product structure can be deduced as well as presence or otherwise of any anhydride or diacyl peroxide of carboxylic acid impurity can be seen by comparison with the spectrum of each possible impurity compound prepared separately. For MMPP itself there can be seen a clear percarboxylic acid peak at 1740 $cm^{-1}$ and carboxylate anion broad peak at 1550–1600 $cm^{-1}$. The anhydride would give peaks at 1770, 1790 and 1850 $cm^{-1}$, an aromatic carboxylic acid peak would occur at 1680–1700 $cm^{-1}$ and for a diacyl peroxide there would be the carboxylic acid peak and two extra peaks between 1755 and 1820 $cm^{-1}$ would occur.

In Examples 14/15, the same route and general method as in Examples 1–13 was followed, but using an 8x scale, and introducing the solids over 20 minutes. Thus, the weight of phthalic anhydride used was 120.4 g and that of 50% hydrogen peroxide was 55.2 g. The weight of magnesium oxide and demineralised water is again specified in Table 1, but in addition the aqueous phase in Example 14/15 contained 15 g isopropyl alcohol which acted to reduce foaming. The process also differed slightly from that employed in Examples 1–13 in that at the end of the reaction period the mixture was cooled to 8° C., filtered and the filtered cake dried at 40° to 50° C. in an oven, without employing an intermediate washing stage with ethyl acetate. In Example 16, the route of Examples 14/15 was followed except that the post-introduction reaction period was 40 minutes instead of about 10–20 minutes.

In Examples 1–10 and subsequent Example 17, the magnesium oxide was of 97.9% purity, had a measured iron content of 6 ppm as Fe and a particle size of below 125 um, 71% less than 63 um. That used in Examples 11 to 13 was an 'Analar' reagent, in Examples 14 to 16 was of 99.7% purity, with an iron content of 10 ppm, both of which comprised particles below 125 um. In Table 1, the ratios PAn:Mg and $H_2O$:Mg represent respectively the mole ratios of phthalic anhydride to magnesium and initial water to magnesium in the reaction mixture, and the term 'solids added' means the weight of anhydride plus base added in grams per 1000 g of aqueous phase.

TABLE 1

| Example Number | MgO g | PAn:Mg | $H_2O$ g | $H_2O$:Mg | Solids Added | Temp °C. |
|---|---|---|---|---|---|---|
| 1 | 2.18 | 1.92:1 | 25. | 30:1 | 540 | 10 |
| 2 | 1.63 | 2.57 | 25. | 40 | 523 | 20 |
| 3 | 1.77 | 2.36 | 25. | 37 | 527 | 20 |
| 4 | 1.90 | 2.20 | 37.5 | 49 | 384 | 20 |
| 5 | 1.90 | 2.20 | 58.3 | 74 | 261 | 20 |
| 6 | 1.90 | 2.20 | 16.7 | 24 | 722 | 20 |
| 7 | 2.18 | 1.92 | 75. | 82 | 210 | 20 |
| 8 | 2.18 | 1.92 | 58.3 | 65 | 264 | 20 |
| 9 | 2.18 | 1.92 | 25. | 30 | 540 | 20 |
| 10 | 2.18 | 1.92 | 16.7 | 21 | 730 | 20 |
| 11 | 2.18 | 1.92 | 25. | 30 | 540 | 30 |
| 12 | 2.45 | 1.71 | 25. | 26 | 549 | 30 |
| 13 | 2.72 | 1.54 | 25. | 24 | 557 | 30 |
| 14 | 17.12 | 1.92 | 285. | 41 | 410 | 40 |
| 15 | 17.12 | 1.92 | 285. | 41 | 410 | 20 |
| 16 | 17.12 | 1.91 | 300. | 43 | 400 | 10 |

TABLE 2

| Ex No | Solid Product | | | Filtrate (Mother Liquor) | | | | Loss of Avox % |
|---|---|---|---|---|---|---|---|---|
| | Weight (g) | Weight % Avox | Weight % Mg | Weight g | Wt % Avox H₂O₂ | Wt % Avox Peracid | Mg | |
| 1 | 17.2 | 5.18 | 5.46 | 22.6 | 0.80 | 1.13 | 1.21 | 16.7 |
| 2 | 16.1 | 5.88 | 4.60 | 22.4 | 1.57 | 1.07 | 0.73 | 5.3 |
| 3 | 17.0 | 6.09 | 4.91 | 20.3 | 1.27 | 0.98 | 0.76 | 8.0 |
| 4 | 16.8 | 6.30 | 4.89 | 35.2 | 0.41 | 0.86 | 0.73 | 7.5 |
| 5 | 11.9 | 5.95 | 4.85 | 62.4 | 0.22 | 1.01 | 0.80 | 9.0 |
| 6 | 19.5 | 6.06 | 4.82 | 9.9 | 1.30 | 0.92 | 0.83 | 13.7 |
| 7 | 5.6 | 5.93 | 3.94 | 86.1 | 0.11 | 0.82 | 0.79 | 15.8 |
| 8 | 12.9 | 6.19 | 4.90 | 60.4 | 0.11 | 0.90 | 0.90 | 13.2 |
| 9 | 18.9 | 6.15 | 5.12 | 22.0 | 0.43 | 1.32 | 0.97 | 9.2 |
| 10 | 21.0 | 6.06 | 5.21 | 11.7 | 0.42 | 1.00 | 1.16 | 5.2 |
| 11 | 17.8 | 6.10 | 5.04 | 20.6 | 0.26 | 0.90 | 1.01 | 18 |
| 12 | 19.8 | 5.30 | 5.49 | 15.0 | 0.47 | 1.05 | 0.86 | 22 |
| 13 | 16.5 | 5.47 | 5.54 | 21.0 | 0.12 | 0.86 | 1.89 | 30 |
| 14 | 109 | 5.08 | 4.94 | 291 | 0.21 | 0.79 | 1.03 | 35 |
| 15 | 165 | 6.05 | 4.90 | 251 | 0.13 | 0.74 | 0.81 | 8 |
| 16 | 148 | 5.88 | 4.95 | 291 | 0.30 | 0.92 | 0.83 | 6 |

When Example 15 was repeated using 25.3 g magnesium hydroxide (9.76%, 15 ppm Fe) instead of the magnesium oxide, 149 g of the product was obtained having an Avox of 6.09%, and 4.67% Mg, the IR spectrum again clearly indicating that MMPP had been formed.

From Examples 1-16, it can be seen that solid magnesium monoperoxyphthalate can be obtained readily using an aqueous reaction medium. From a detailed comparison of the results, it will be observed that the optimum temperature for reaction is in the region of 20° C. in that there is a tendency for the loss of avox from the system to increase at higher temperatures of, for example, 30° or 40° C. It will be observed that the product can be obtained employing ratios of phthalic anhydride to magnesium base over a wide range of from 1.5:1 to 2.6:1, but at the highest ratio, 2.57:1, the product was contaminated with phthalic anhydride and phthaloyl peroxide to a detectable extent. However, at slightly lower ratios of 2.36:1 or lower there was no detectable phthalic anhydride or diphthaloyl peroxide since the apparent excess of anhydride remained in solution as unneutralised peracid. From the results it will also be observable that solid products having a high avox content were obtained employing water to magnesium ratios in the range from about 20:1 to about 80:1.

EXAMPLE 17

In Example 17, the process of Example 15 was repeated using the same grade of reagent except for magnesium oxide which was the same as that used in Example 1, and subsequently the greater part of the mother liquor was recycled in a sequence of process steps comprising on the first recycle (i) measurement of residual peracid, peroxide and magnesium concentrations (ii) calculation of the equivalent amount of phthalic anhydride and of the amounts of fresh reagents to be added to closely reproduce the conditions in the initial cycle, i.e. mole ratios of phthalic anhydride to magnesium and to hydrogen peroxide and water to magnesium, and to produce a similar weight of product per unit volume of reaction medium, (iii) addition of the hydrogen peroxide and water (iv) addition of the solid reagents over 20 minutes and post introduction reaction for another 10 minutes, as in the initial cycle and (v) solid/liquid separation. In subsequent cycles the residual levels were monitored but the same calculated amounts of fresh reagents as in the first recycle stage were used.

In the initial cycle, the amounts of reagents used comprised water (312.6 g in total) isopropyl alcohol (15 g), hydrogen peroxide (27.6 g) phthalic anhydride (120.4 g) and magnesium oxide (17.5 g). In each recycle, the respective amounts were mother liquor (270 g), water (86.8 g), hydrogen peroxide (22.5 g) phthalic anhydride (100 g) and magnesium oxide (13.8 g). The results of the initial cycle and typical recycles 3, 5 and 7 are shown in Table 3.

TABLE 3

| Cycle No. | Solid Product | | | Filtrate (Mother liquor) | | |
|---|---|---|---|---|---|---|
| | Wt. g | Wt. % avox | Wt. % Mg | Wt. g | Wt. % avox H₂O₂ | Wt. % avox Peracid | Mg |
| 1. | 154 | 6.32 | 4.91 | 287 | 0.09 | 0.68 | 0.83 |
| 3. | 159 | 6.06 | 4.90 | 282 | 0.14 | 0.68 | 0.84 |
| 5. | 152 | 6.10 | 4.86 | 297 | 0.23 | 0.83 | 0.84 |
| 7. | 159 | 6.15 | 4.88 | 297 | 0.30 | 0.82 | 0.79 |

From Table 3, it can be seen that a substantially steady state had been achieved in the amount and quality of the product and the filtrate (mother liquor) with the exception of hydrogen peroxide concentration which was rising slowly, indicating that very slightly less (about 1%) peroxide was needed. The iron content in the filtrate after the last cycle was measured at only 8 ppm.

EXAMPLE 18

In this Example, the general method of Example 16 was followed, with the exception that magnesium carbonate (41 g, 89.2% purity, Fe 13 ppm) was employed instead of the magnesium oxide. The solids were introduced over a period of 30 minutes and the post-introduction reaction period was 45 minutes. The resultant product was obtained in an amount of 138 g solid having an avox content of 6.02% and magnesium content of 5.14%. The filtrate was obtained in an amount of 307 g having an avox content in the form of H₂O₂ of 0.11% and in the form of peracid of 0.88%, and a magnesium content of 0.91%. The overall loss of avox from the system was 12%.

From this Example it can be seen that magnesium carbonate can be employed instead of magnesium oxide with a broadly similar result being obtained.

EXAMPLE 19

In this Example, magnesium acetate tetrahydrate (21.1 g, 0.099 moles) was introduced with stirring into a solution of aqueous hydrogen peroxide (7.73 g, 0.197 mole $H_2O_2$, 86.7% w/w) and demineralised water (2.58 g) forming a slurry. Phthalic anhydride (30 g, 0.203 moles) was stirred into the slurry over a period of 20 minutes, the reaction mixture being maintained then and during the subsequent reaction period of about 15 minutes at a temperature of 22° C. At the end of the reaction period the mixture began to dry as magnesium monoperoxyphthalate crystalised out. The eventual product was completely dry, and this was then washed with a small volume of ethyl acetate and dried. The resultant product had an avox of 6.05%, a magnesium content of 4.95% and a total weight of 42.8 g. Further analysis of the product indicated that, either present as such or in the form of the peroxyacid derivative, the product contained 68.1% phthalate calculated as phthalic acid and 2.6% acetate, calculated as acetic acid. The water content for the product was equivalent to a mole ratio of water to magnesium of approximately 5:1.

From this Example, it can be seen not only that it is possible to obtain a product in dry form in a single step, all the residual water being retained by the product as an hydration product, but that the process can employ as a magnesium compound the salt of a weak acid.

EXAMPLE 20

In this Example, finely ground phthalic anhydride (28.8 g, 0.195 moles) and magnesium oxide (97.9% purity, 15 ppm iron content, 4.16 g, 0.168 moles) were thoroughly mixed in the dry state and to that mixture was added rapidly aqueous hydrogen peroxide (35% w/w, 0.171 moles $H_2O_2$). The mixture was thoroughly stirred, giving in appearance an initial damp powder that changed first to a liquid phase of low viscosity and then to a thick cream during a period of about 20 minutes, during which the temperature was maintained at approximately 20° to 25° C. by cooling in an ice/water bath. The thick cream was then cooled to approximately 5° C. and by the end of about 2 minutes the mixture solidified to an essentially dry solid mass. The solid mass was then gently crushed to break it up, washed with ethyl acetate (100 mls) and air dried giving a white powder. On analysis, the product weighed 33 g and had an avox content of 4.39%, and appeared to contain detectable amount of phthalic anhydride. Upon further washing, with chloroform, the phthalic anhydride was removed to a considerable extent and the resultant product had an avox of 5.62%.

When this Example was repeated but using 0.195 mole of succinic anhydride or 0.195 mole of hexahydrophthalic anhydride instead of the phthalic anhydride, and adding solids to a liquid mixture instead of vice versa the resultant solid was substantially free from peroxyacid, i.e. did not contain the desired product, thereby demonstrating the non-equivalence of classes 1 and 3 with class 2 and succinic anhydride-derived compounds.

EXAMPLE 21 AND COMPARISON C22

In this Example and in this comparison, particulate phthalic anhydride (60.2 g) was blended with a commercial particulate magnesium oxide (9.75 g, 87.53% MgO and Fe impurity of 152 ppm) and added over 20 minutes to aqueous hydrogen peroxide (28.25 g, 48.85% w/w $H_2O_2$) diluted with 140 mls demineralised water (DMW) plus a solution of disodium EDTA in either DMW (10 mls, 0.1M) as in Ex 21 or 10 ml DMW as in comparison C22, with stirring and cooling to 20° C. which was maintained for a further 20 minutes. The reaction mixture was then cooled to about 8° C., filtered, and dried. On analysis, the product of Example 21 (71.6 g) analysed as 5.95% Avox, 4.88% Mg and clearly was MMPP from the IR, whereas the solid in comparison C22 had no Avox and comprised phthalic anhydride.

EXAMPLE 23

In this Example, dry mixed magnesium oxide (98% MgO, 13 ppm Fe; 2.09 g, 50.8 mmol) and pyromellitic dianhydride (11.67 g, 55.0 mmol) was added to a solution of hydrogen peroxide (4.18 g of 85% w/w, 105 mmol+25 g DMW). The temperature was kept below 20° C. throughout addition. A creamy suspension was formed which left at below 10°.C. for 1.5 hr. The magnesium peroxypyromellitate was then filtered off, washed with ethyl acetate and air dried. The yield was 10 g, 3.8% Avox, which contained clearly peroxyacid and carboxylate groups.

EXAMPLE 24

In this Example dry mixed magnesium oxide MgO, 13 ppm Fe; 2.05 g, 49.9 mmol) and maleic anhydride (9.97 g, 10.2 mmol) was added to a solution of hydrogen peroxide (4.07 g of 85%, mmol+9.0 g DMW). The temperaturee was generally maintained at 20° C. though it did reach briefly 30° C. at the start of the addition. The mixture thickened 5 minutes after all the reagents had been added. The product, magnesium monoperoxymaleate, was filtered, washed with ehtyl acetate and then air dried. The yield was 14 g, 6.34% Avox, and clearly contained peroxyacid and carboxylate groups.

EXAMPLE 25

50% hydrogen peroxide (13.8 g, 203 mmol) was diluted with 31.7 g DMW and 1.7 g isopropanol. Citraconic anhydride (22.77 g 203 mmol) was added dropwise over 15 min during which time 4.28 g magnesium oxide (99.7%, 10 ppm Fe; 106 mmol) was also added. The temperature was maintained 20° C. Reaction was continued for a further 20 min. The product, magnesium monoperoxycitraconate was filtered off and dried at 45° C. the yield was 16.45 g, having 4.64% Avox, 6.03% Mg, and clearly contained peroxyacid and carboxylate groups.

EXAMPLE 26

In this Example, the effect of extra free iron in the reaction mixture was demonstrated, as could happen if the water used were contaminated.

Each run was effected at the same scale as and employing the same process conditions as comparison C22, but using a magnesium base a sample having an iron impurity of 3 ppm in an amount of 8.75 g, (99.5% MgO) and diluent water that contained varied concentrations of ferrous or ferric iron, which are expressed in terms of the weight iron per weight of Mg base added, ferric in A, B, C, D and ferrous in E, F. The results are summarised in Table 4, in which NM indicates that a measurement was not made and a—that none was detected.

TABLE 4

| Run | Total Fe ppm | Product Characteristics | | | | |
|-----|------|--------|------|------|------|------|
| | | Amount g | Avox % | Mg % | IR trace CO$_2$H | Anhydride |
| A | 8 | 70.3 | 6.04 | 4.91 | weak | — |
| B | 13 | 70.0 | 5.33 | NM | strong | — |
| C | 23 | 35.8 | 4.35 | 4.32 | strong | strong |
| D | 53 | NM | — | — | | totally |
| E | 23 | 63.1 | 5.17 | 4.23 | strong | strong |
| F | 153 | NM | — | — | | totally |

From Table 4, it can be seen that increasing iron contents lead progressively to a product having a diminished peroxyacid content which eventually is zero. Secondly, it can be seen that ferrous impurity can be tolerated slightly more than ferric impurity, but of course in recycle operations, the ferric/ferrous equilibrium would be firmly to the ferric side in such an oxidising environment. To all practical intents, run A is tolerable, runs B and E are verging on being tolerable but runs C, D and F are unacceptable.

We claim:

1. In a process for the production of a solid hydrated magnesium salt of an aromatic or conjugated aliphatic compound containing peroxycarboxylic acid group and a carboxylate group, said process comprising reacting an anhydride, a magnesium base, water and hydrogen peroxide to form said magnesium salt, the improvement wherein:

said reaction is carried out in an aqueous phase reaction medium;

said anhydride is selected from those which form a compound selected from classes 1 and 3 set forth hereinafter:

Class (1)-aromatic carbocyclic compound substituted around the aromatic nucleus by a carboxylate group and a peroxycarboxylic acid group both groups being derivable from the corresponding aromatic carbocyclic anhydride by reaction with hydrogen peroxide, said aromatic carboxylic compound optionally being further substituted by at least one of the groups selected from alkyl, carboxylate, sulphonate, nitro, chloro and bromo groups and Class (3)-olefinically unsaturated aliphatic percarboxylic acid in which the carbonyl group of the peroxycarboxylic acid substituent is conjugated with the carbonyl group of a carboxylate substituent via olefinic unsaturation which carboxylate and peroxycarboxylic acid substituents are derivable from the corresponding anhydride by reaction with hydrogen peroxide; and, the content of free iron in said aqueous phase reaction medium is sufficiently low that solid hydrated magnesium salt of the carboxylate group precipitates out.

2. A process according to claim 1 employing at least 100 g anhydride and magnesium base per 1000 g aqueous phase.

3. A process according to claim 2 employing hydrogen peroxide in an equivalent mole ratio to the anhydride of from 0.9:1 to 2:1.

4. A process according to claim 3 in which the equivalent mole ratio of hydrogen peroxide to anhydride is from 0.95:1 to 1.2:1.

5. A process according to claim 2 employing an equivalent mole ratio of anhydride to magnesium base of from 1.5:1 to 2.5:1.

6. A process according to claim 5 in which the equivalent mole ratio of anhydride to magnesium base is from 1.8:1 to 2.2:1.

7. A process according to claim 2 in which aqueous phase reaction medium separated from the solids is analysed for peroxyacid, hydrogen peroxide and magnesium contents and is recycled, and in the subsequent cycle further amounts of anhydride, magnesium base and where necessary hydrogen peroxide are added to the aqueous phase reaction medium.

8. A process according to claim 7 in which the anhydride, magnesium base, hydrogen peroxide and water are introduced into the recycled aqueous phase reaction medium in equivalent mole ratios of anhydride to magnesium base of 1.8 to 2.2:1; hydrogen peroxide to anhydride of 0.95 to 1.2:1, and water to magnesium base of 5 to 12:1 respectively.

9. A process according to claim 1 in which the aqueous phase reaction medium comprises equivalent mole ratios of (a) anhydride, (b) hydrogen peroxide and (c) total water to the magnesium base in the ranges of respectively (a) 1.5:1 to 2.5:1, (b) 1.5:1 to 3.0:1 and (c) 5:1 to 12:1.

10. A process according to claim 1, 7 or 9 in which the aqueous phase reaction medium is maintained at a temperature of not more than 30° C.

11. A process according to claim 10 in which the aqueous medium reaction medium mixture is maintained at a temperature of 5° to 25° C.

12. A process according to claim 1, 7 or 9 in which the free iron content of the magnesium base is not more than $25 \times 10^{-6}$ moles of iron per mole of base.

13. A process according to claim 1, 7 or 9 in which the magnesium base and anhydride are introduced into the aqueous phase reaction medium containing hydrogen peroxide and maintained in contact during a period in total of 20 to 150 minutes.

14. A process according to claim 1, 7 or 9 in which the anhydride is phthalic anhydride.

15. A process according to claim 1, 7 or 9 in which the magnesium base is magnesium oxide, hydroxide, carbonate or basic carbonate.

16. A process according to claim 15 in which the free iron content of the magnesium base is not more than $25 \times 10^{-6}$ moles of iron per mole of base.

17. A process according to claim 1, 7 or 9 in which the amount of reactants added produces a slurry having a solid product content on a dry weight basis of from 15% to 45%.

18. A process according to claim 2 or 8 in which phthalic anhydride is reacted with a magnesium base selected from the group consisting of magnesum oxide, hydroxide, carbonate and basic carbonate, the free iron content of which is not more than $25 \times 10^{-6}$ moles of iron per mole of base and hydrogen peroxide at a temperature maintained in the range of 5° to 25° C., for a period of contact selected in the range of 20 to 150 minutes.

19. A process according to claim 1 wherein the anhydride and magnesium base are employed in an equivalent mole ratio of 1.5:1 to 2.5:1 and in a total amount of at least 100 g per 1000 g aqueous phase, the aqueous phase comprises at least 0.7 moles hydrogen peroxide per mole of anhydride and at least 5 moles water per mole of magnesium base, and the water content of free iron in the reaction mixture is less than $45 \times 10^{-6}$ moles per mole of magnesium base.

* * * * *